United States Patent [19]
Young

[11] Patent Number: 5,665,058
[45] Date of Patent: Sep. 9, 1997

[54] ORTHOSIS FOR THE SHOULDER AND ARM

[75] Inventor: David Ernest Young, Watlington, United Kingdom

[73] Assignee: Innovative Care Limited, Abingdon Oxon, England

[21] Appl. No.: 509,296

[22] Filed: Jul. 31, 1995

[30] Foreign Application Priority Data

Apr. 13, 1995 [GB] United Kingdom ............ 9507724

[51] Int. Cl.[6] .................................................. A61F 5/00
[52] U.S. Cl. ........................... 602/20; 602/4; 602/16
[58] Field of Search .................... 128/877, 878, 128/881; 602/4, 5, 16, 19–21

[56] References Cited

U.S. PATENT DOCUMENTS 1,976,244  10/1934  Moran .......................... 602/20 X
4,241,731  12/1980  Pauley ............................ 602/4
4,299,210  11/1981  Santy ............................. 602/19
4,373,517  2/1983  Criscuolo ...................... 602/20 X Primary Examiner—Linda C. Dvorak
Attorney, Agent, or Firm—Tilton, Fallon, Lungmus

[57] ABSTRACT

An improved orthosis provides mobilization of the shoulder joint and arm in a wide variety of clinically useful positions and also optional controlled movement of the forearm over a selectable range in the vertical plane. The orthosis has waist securing and harness means for securing it to the human body. A rise and fall mount attached to a waistband supports a pivoting slide and a forearm support assembly which includes a hand support. An arrangement of slides and adjustable securing means is so disposed as to allow the shoulder orthosis to be configured rapidly, easily and in a continuously variable manner for rigid, stable immobilization following injury or surgery.

5 Claims, 8 Drawing Sheets

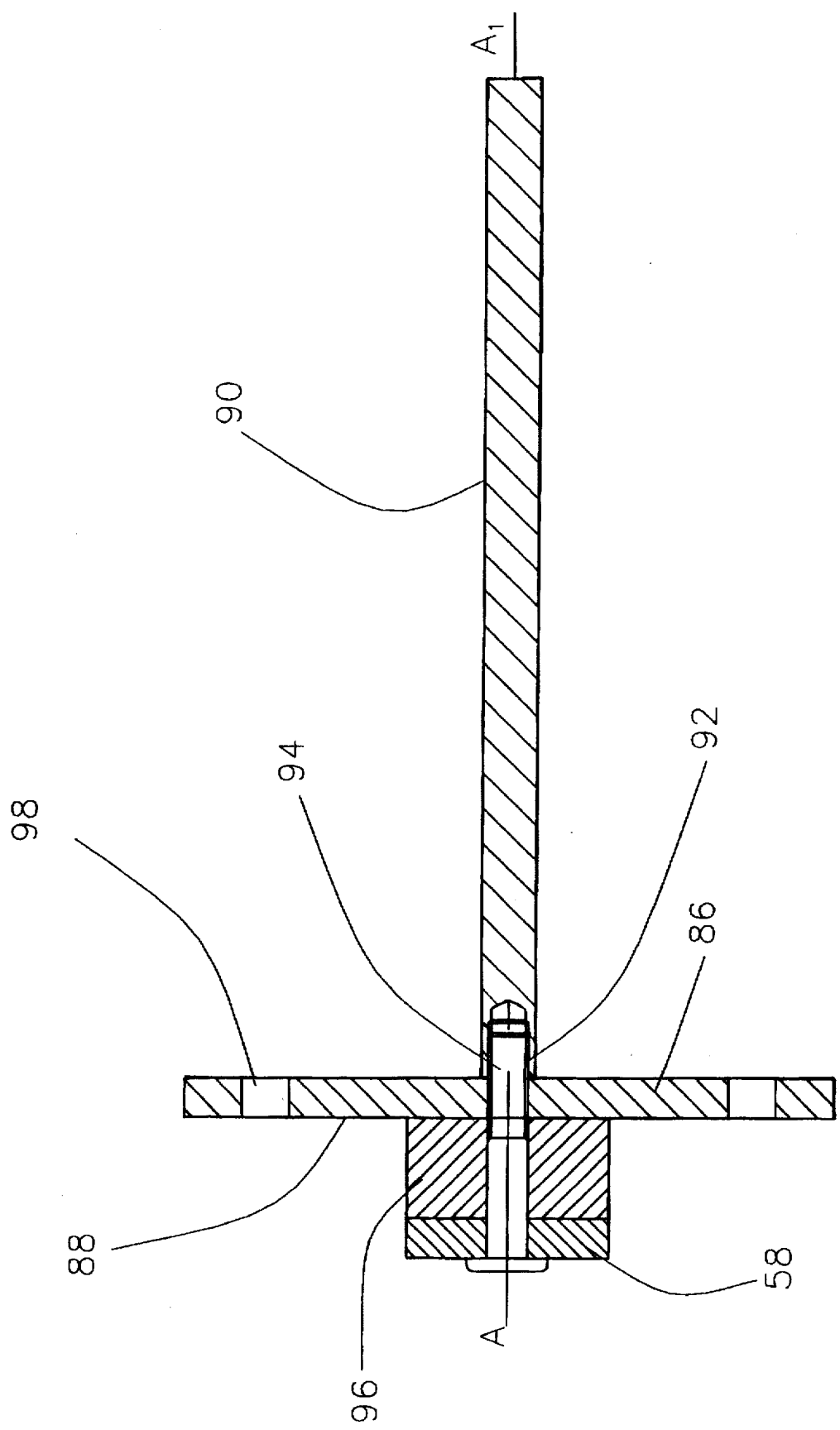

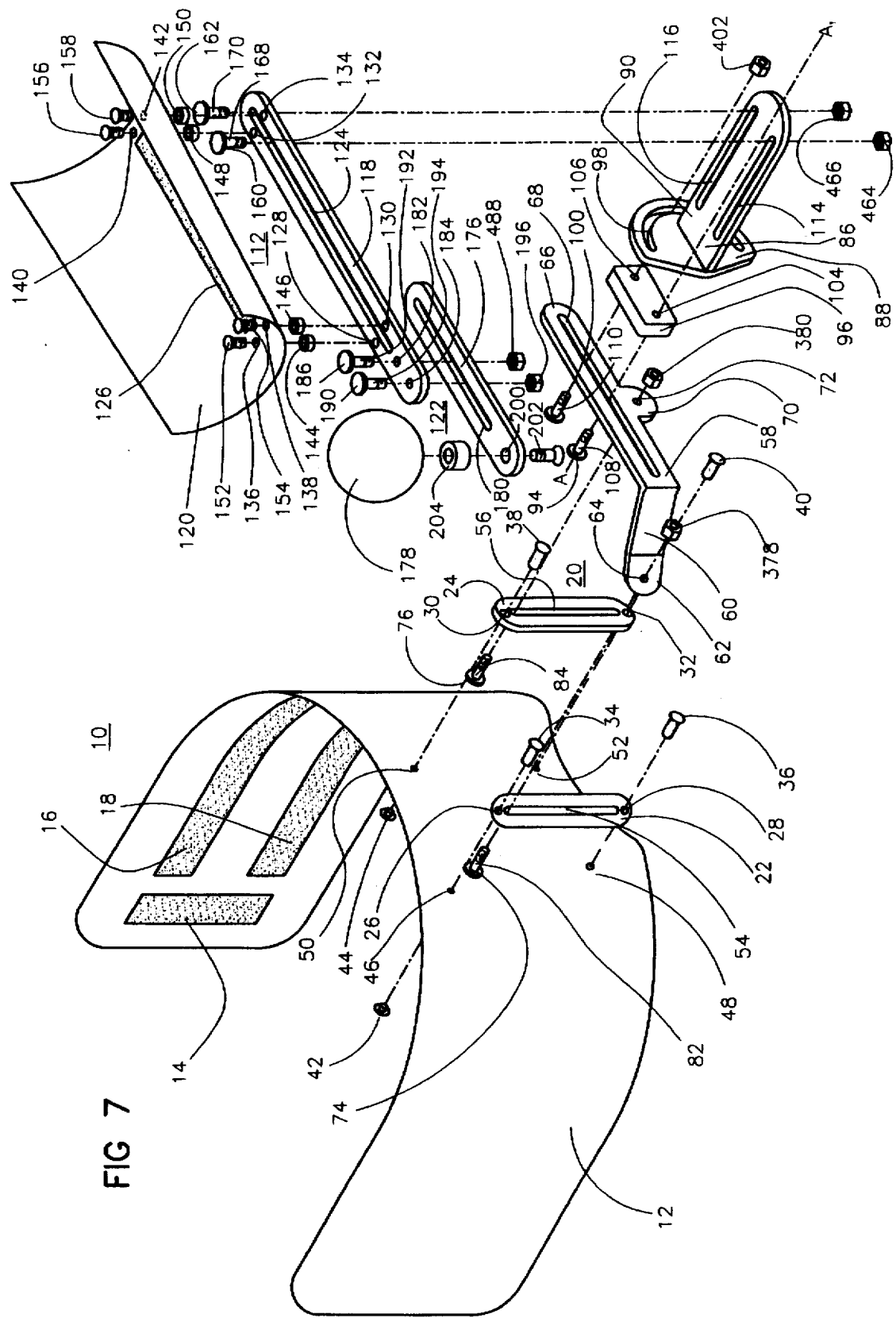

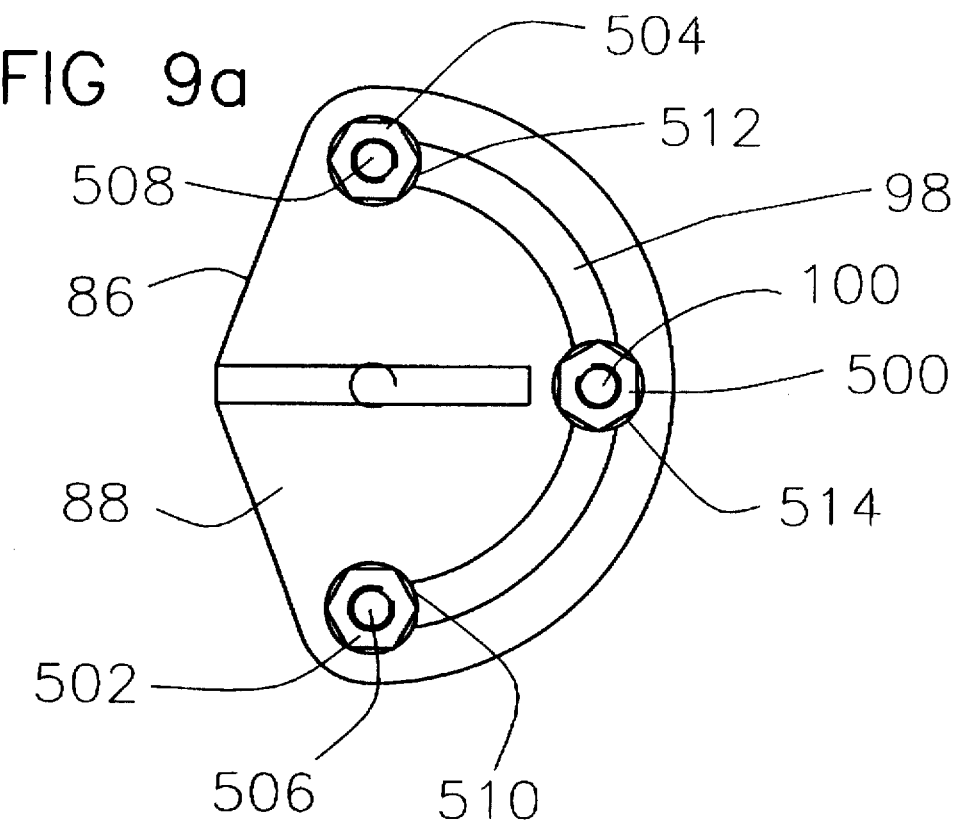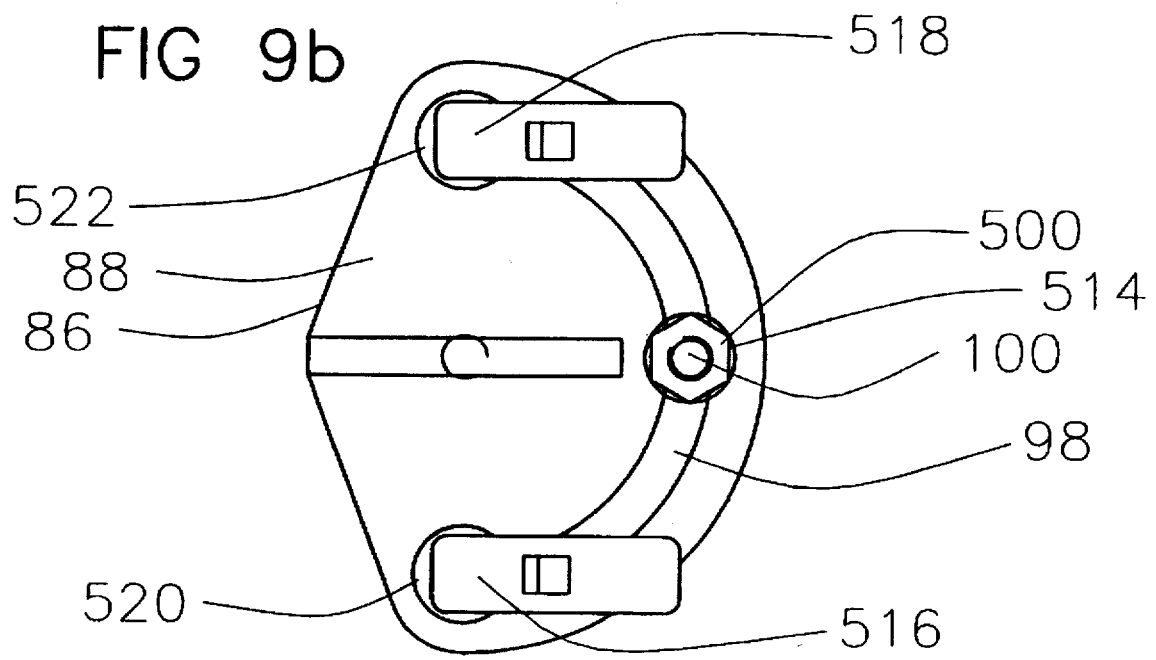

ORTHOSIS FOR THE SHOULDER AND ARM

BACKGROUND AND SUMMARY

This invention relates to devices, including orthopedic braces and splints, for the shoulder joint and arm where it is generally but not exclusively desired to provide a fixed position for the arm relative to that joint. These devices are generally referred to by those skilled in the art as braces or orthoses. Many joint injuries and treatments require an orthosis of a type which provides early controlled motion through a pre-selected range after or in conjunction with other treatment. The shoulder joint is no exception to this general rule. However, there are also many conditions and treatment modalities where early mobilization is not favored and rigid immobilization is used, placing the arm and the joint in carefully selected relative positions during a period of rehabilitation following injury or surgery.

Both mobilizing and immobilizing orthoses must, necessarily, be designed with architecture appropriate to the normal physiological limits of angular travel of the joint to be treated and to the linear travel of associated limbs and the planes in which this occurs. These considerations should dictate the limits of movement and adjustment to be provided by the orthosis. The normal shoulder joint is capable of movement in multiple planes and this increases the degree of difficulty for the orthosis designer, especially since it is generally required to include control of the arm. This is necessary because the arm can exert considerable leverage at the shoulder joint. Shoulder joint movements include flexion, extension, abduction, adduction and internal and external rotation. All are possible over a large angular range and in numerous combinations. On the other hand the shoulder joint is not weight bearing in the sense that the knee or hip are compressively loaded and this does confer some design latitude.

Until recently, orthotic design for the lower limb was more intensive and wide ranging than for the upper limb. The reasons are fairly obvious in that structural or dynamic failure of the hip or knee directly impairs or prevents mobility. Similar failure in the upper limb leads to severe but less disabling sequelae. Notwithstanding this, there are numerous injuries due to trauma and overuse which can, in damaging the upper limb, markedly restrict or incapacitate the sufferer. A damaged shoulder can, for instance, make dressing, driving or writing difficult or even impossible.

Treatment of shoulder injuries by arthroscopic surgical techniques has grown rapidly over the last decade and leading authorities predict that surgical advances will continue for some years to come. The public, including the older patient population, now has increased expectations of a satisfactory functional resolution of shoulder joint problems. The trend of increasing demand for surgery on the shoulder, together with adjunctive treatment, will probably be maintained and this should be seen against the fact that even by 1989, the shoulder was indicated by the American Academy of Orthopaedic Surgeons as the reason for 14% of all consultations leading to surgery.

The present invention is concerned with conditions of the shoulder which, whatever the primary method of treatment, are managed post-operatively or following injury mainly by immobilization in a selected position but where, in some cases or at some stages, an option for early mobilization of the forearm would be useful. Recurrent posterior subluxation of the shoulder is an example of a condition which is often treated by surgery, usually followed by a period of immobilization.

A need exists for an orthosis which is light and stable and in which adjustments can be made in a continuously variable manner in relation to all directions of movement which occur in the human shoulder. Such an orthosis should provide sufficient linear adjustment for the arm to induce angular displacement of the shoulder joint to any selected position over a large clinically useful range. It is desirable that such an orthosis should be wearable while ambulatory but also readily tolerable while sitting or lying in bed. It to these needs that the present invention is directed.

The simplest orthoses which provide immobilization of the shoulder fall into two categories. Abduction pillows, as the name implies, provide abduction at a more or less fixed position and an example of this type, though not the simplest realization, is disclosed in Scott, U.S. Pat. No. 4,896,660. Orthoses of this type are bulky and can inconvenience the ambulatory patient, particularly in restricted places such as doorways. However, abduction is not always required and simple shoulder immobilizers, which comprise a cotton or canvas sling for the lower arm and elbow together with suitable straps, are frequently used in relatively straightforward situations. Examples of this type, though once again not the simplest, include Scott, U.S. Pat. No. 4,878,490 and Florek, U.S. Pat. No. 4,480,637.

A more complex class of shoulder orthoses might be called the "pylon" type. This class is provided with a waist-worn member upon which a generally upwardly directed bar or pylon is mounted. A suspension harness is worn on the contra-lateral shoulder and a mechanism is positioned in the axilla in order to provide support and positioning means for the shoulder joint. The axillary mechanism sometimes also provides means for control over a selectable range for one or more motions of the shoulder. The earliest example of this general type we have found was disclosed in Maddox, U.S. Pat. No. 1,340,630 in 1920 and other examples and variants include Brudny, U.S. Pat. No. 4,417,569 and Johnson, U.S. Pat. No. 5,360,391. The use of a pylon proximate the trunk and an axillary mechanism is also sometimes seen in continuous passive motion apparatus for the shoulder as in Funk, et al., U.S. Pat. No. 4,651,719.

The authors of the present invention have previously been granted letters patent (U.S. Pat. No. 5,033,461, EPO 0,404, 362 and U.S. Pat. No. 5,046,490) in respect of various devices for bracing and providing control of movement at the shoulder. The mechanisms described therein have been used commercially in a shoulder orthosis for the control of movement in a continuously variable manner, in the included angle between the arm and the trunk. The device is made by Protectair Limited of Abdingdon, U.K. and is sold under the name Masterhinge® Shoulder Brace. The gross morphology conforms to the general description of a "pylon" type orthosis outlined above.

Other orthoses of this general type include two shoulder positioning devices made by United States Manufacturing Company of Pasadena, Calif., U.S.A. The products are known commercially as the SASI® and SASII®. They offer positioning but not control of range of motion in abduction and adduction.

Another shoulder orthosis of this type is made by Donjoy Inc. of Carlsbad, Calif., U.S.A. and is sold under the commercial name Quadrant®. This orthosis provides adjustment for position of the shoulder in abduction but does not provide for controlled movement in abduction.

A "pylon" type orthosis is known to have been offered by Hug GmbH, Germany in the late 1980's and employed a rubber compression element in the axilla. Some abduction movement appears to have been possible but so far as is known, this was not over a controlled range.

The earliest commercial product of the "pylon" type we are aware of was an orthosis believed to have been made by Durr-Fillauer Incorporated of Chattanooga, Tenn., U.S.A. and possibly called the Toronto Shoulder Orthosis. This offered selected fixed shoulder positions in abduction and free movement or a fixed position in flexion.

Another class of shoulder immobilizing orthoses might be referred to as the "non-pylon" type. Members of this class do, generally, have a waist-worn member but they do not have a pylon and axillary mechanism. This is the general class to which the present invention belongs.

One example is made by the United States Manufacturing Company of Pasadena, Calif., U.S.A. and is sold under the commercial name Gunslinger®. This orthosis does not provide abduction positioning whereas a variant, called the GunslingerII®, employs an outrigger by means of which 45° of abduction may be achieved. However, this latter orthosis appears to be recommended for abduction only. Both versions employ manually tightened screw clamps which require considerable tightening torque and therefore strength in order to achieve stability of adjustment. There are two adjustments which appear to allow or affect shoulder rotation. One adjustment employs a simple, manually tightened, screw operating a pinch clamp on a circular-section spigot. The clamp might be vulnerable to under-tightening which could lead to instability on the circular mount. This would be undesirable in a shoulder joint which had recently been operated upon. The other adjustment involves a substantially circular plate which can be moved along concentric slotted paths, close to its circumference and is manually secured by tightening two screw clamps. The spigot of the first referred to adjustment is mounted on the circular plate near its edge close to what is, effectively, the upper pole thereof. It seems inevitable, therefore, that any adjustment along the circular path which the plate must follow will produce a variable displacement of those parts of the device which support the forearm. This will cause the position of the shoulder joint to be varied with both a vertical and either an anterior or posterior component, at the same time. It is difficult to relate this compound adjustment to the anatomy of the structures presumably under treatment and to any direct physiological requirement.

In Burkhead, et al., U.S. Pat. No. 5,385,536, there is disclosed another "non-pylon" device which has an outrigger arrangement. This has a waistband (described as a saddle) secured on the waist with straps and stabilized with a contra-lateral shoulder strap. The saddle is provided with a discontinuous vertical mounting rack for a positioning rod. The positioning rod is used for varying the elevation of the arm with coarse and fine adjustments for length and it has universal joints at the upper and lower ends. A single axis elbow hinge has arms which may be locked with a pin and means are provided for retaining both the upper and lower arm. Means for retaining and supporting the hand and wrist are not disclosed. Coarse adjustment of the length of the positioning rod, which has telescoping inner and outer elements, is discontinuous and is effected by means of a locking pin traversing both elements. The lower ball joint is locked by a compression nut and locking of the upper ball joint is by compression delivered by means of threadedly compressing two elements of a socket housing against the ball with another nut.

Ball joints as a means of positioning a joint are notorious in the art of orthotics for their tendency to be unstable and to lose position. This is especially so where narrow circular line contacts are employed between the ball and the locking means, as in the case of the lower ball joint employed in the Burkhead device. In the art, ball joints are normally chosen in situations where it is not necessary or not desirable to lock or block movement at a particular position. Where they are chosen and must be locked, a substantially enclosed design is normally selected, however, this tends to limit the angular operating range of the mechanism because so much of the ball is within a housing. In this case, the need to achieve a large angular range of adjustment is clear. That stability is also recognized as important may explain why relatively massive locking nuts are illustrated for the preferred embodiments—much bigger across flats than the diameter of the ball of the joint. The risk is that these may be over-tightened with a significant possibility of damage or excessive wear to components. An additional limitation of the Burkhead device is that the positioning assembly requires a substantial minimum length in order to achieve worthwhile elevation of the arm in a large population of patients. This must necessarily limit the capacity for the arm to be brought close in to the body with the shoulder abducted. It also partially negates one purpose of a vertical positioning mount on the saddle which presumably is to accommodate variation in the length of the humerus. Finally, as with the Gunslinger® device, described above, movement of the forearm into scandent or dependent positions appears to involve compound adjustment of the shoulder joint position, in this case due to the upper ball joint being distanced from the position of the elbow joint by an element called an arm.

Williams, U.S. Pat. No. 3,952,733 discloses an arm support which in some respects appears to be a hybrid of the "pylon" and "non-pylon" types of orthosis.

Considering other types of device in the art, in Lipton, U.S. Pat. No. 5,000,168, there is disclosed a portable limb supporter which employs two or more, telescoping, discontinuously adjustable, positioning assemblies, the upper and lower ends of which are pivotally attached to other elements by yoke joints. Stability on the waist would appear to be limited and there are no apparent means for medial and lateral adjustment.

A hand forearm support disclosed by Meals, U.S. Pat. No. 4,807,609, appears to accommodate rotation of the forearm which may well allow rotation at the shoulder, however, means for elevating the arm are not disclosed and the use of a support for this purpose, such as table, is required.

In U.S. Pat. No. 5,231,998, there is disclosed an orthosis for dampening limb tremors which allows functional activities of the arm, over a range of motion, in a seated patient. The device requires a support, such as a wheelchair and means for attachment to the body are not disclosed. This patent is particularly directed towards sensor and braking means for an orthosis with multiple degrees of freedom and is referenced as of general interest to those active in the art of orthotics for the upper limb.

The present invention provides an improved shoulder and arm positioning orthosis to be used following injury or surgery. In the invention, a novel arrangement between a rise and fall mount, a pivoting slide and a forearm support assembly induces a very large angular range of positions for the shoulder joint in a plurality of planes by providing a large and continuously variable linear range of adjustment for the arm. Additionally and optionally, the orthosis of the present invention provides for controlled movement of the forearm over a selectable range. The orthosis of the present invention is light and particularly provides for improved ease of adjustment and stability in an ambulatory patient and may also be worn while sitting or lying down.

According to a first aspect of the invention, there is provided an orthosis for the human shoulder joint and arm which provides securing means having buckle, strap harness, belt, buckle, strap and lining means for securing it to the human body in a stable, secure and comfortable manner.

According to an important aspect of the invention, there is provided a stable rise and fall mount, for other functional elements of the orthosis, which is secured to the waistband and as the form of two, similar, slotted metal bars in substantially parallel and vertical alignment, together with a third metal bar in the form of an asymmetrical, angled bracket. The angled bracket, which has a slotted, laterally disposed and an antero-posteriorly directed portion is adapted for receiving adjustable attachement means for adjustably securing it, disposed in substantially horizontal manner, to each of the vertical bars. Adjustable securing means are conveniently but not necessarily, in the form of lever-operated, pre-set, quick-release, over-center clamps attached, not-releasably, by bolt means. By slackening the clamps, the angled bracket may be moved, in a continuously variable manner, to any position within the slots of the vertical bars, after which the clamps are re-tightened. Other elements of the orthosis and an arm held within it may thus be located at a selected position in the vertical plane.

According to another important aspect of the present invention, there is provided a metal pivoting slide having a generally disposed pivoting plate and a lateral slide support. The pivoting slide is centrally, pivotally and non-releasably secured to the slot of the angled bracket of the rise and fall mount with a pivot bolt. The pivoting plate is provided with an arcuate slot.

Bolt means, disposed within the arcuate slot and the slot in the angled bracket, threadedly and non-releasably engage with adjustable securing means, similar to those employed in the rise and fall mount and thereby secure the latter to the pivoting slide. Spacing means, disposed between the pivoting plate and the angled bracket, prevent interference between elements of releasable securing means and other parts of the mechanism. The elements of the pivoting slide cooperate with the rise and fall mount to provide pivotal and antero-posterior adjustment means for a forearm support assembly mounted upon the lateral slide support. By slackening releasable securing means, the pivoting slide and forearm support assembly may be positioned, in a continuously variable manner, at any point along the slot of the angled bracket of the rise and fall mount. These elements may also be moved pivotally, in a continuously variable manner, about the axis of the pivot bolt, to provide a plurality of scandent and dependent positions for a human forearm.

According to another important aspect of the present invention, a forearm support assembly has a slotted, metal travelling support bar, upon which is mounted a lined forearm retaining shell and to which is attached a hand support assembly. Straps pass around the forearm shell to secure the forearm. The travelling support bar is non-releasably secured to the lateral slide support of the pivoting slide with bolt means and adjustable securing means. Bolt means engage intimately with the slot in the travelling support bar and non-intimately with the slots of the lateral slide support. The slots, adjustable securing means and bolt means co-operate to provide a wide and continuously variable range of slidable and lockable adjustment for the forearm assembly of the orthesis. This arrangement, in conjunction with the rise and fall mount, allows the shoulder joint to be abducted to 45° or to be fully adducted. Additionally, anterior, posterior, inswing and outswing adjustments for the arm over a large linear range are possible. A hand support assembly is adjustably, slidably and non-releasably secured to the travelling support bar with bolt means and adjustable securing means. The hand support assembly has a slotted metal hand support bar and a hand support, such as a suitably sized sphere. The hand support assembly, in conjunction with other elements of the forearm support assembly, provides slidably adjustable and lockable means for comfortable positioning for a hand and wrist within the orthosis.

According to another aspect of the present invention, the additional, optional provision of adjustable abutment stop means in the arcuate slot above and below adjustable securing means allows controlled movement of the pivoting plate and hence for a forearm secured within a forearm support assembly.

Within the present invention, the mechanical and geometrical relationship between the components of a rise and fall mount, a pivoting slide and a forearm assembly, particularly slots therein, together with the provision of adjustable securing means, cooperate to allow continuously variable, stable positioning of a human shoulder joint in flexion, extension, internal and external rotation, abduction and adduction or combinations thereof. All may be achieved over a large angular range and in an easy manner. In addition, components are so sized that mutual adjustment between them is adequate to accommodate a very wide range of patient sizes and shapes with a single orthosis for a right arm and shoulder and a single orthosis for a left arm and shoulder.

It is, therefore, an object of the present invention to provide an orthosis for immobilizing an arm and shoulder which will allow the shoulder joint to be positioned accurately over a broader and larger range of angular positions including in flexion, extension, internal and external rotation, abduction and adduction or rational combinations thereof, than with the prior art orthoses.

It is another object of the present invention to provide an orthosis for an arm and shoulder which will allow the arm to be positioned accurately over a larger linear and angular range than with prior art orthoses.

It is another object of the present invention to provide an orthosis for an arm and shoulder which will allow the arm, elbow joint and shoulder joint to be positioned more stably than with prior art orthoses.

It is yet another object of the present invention to provide an orthosis for an arm and shoulder, the adjustable elements of which can be unlocked, adjusted and re-secured easily and without the need for great strength.

It is yet another object of the present invention to provide an orthosis for an arm and shoulder which will, optionally, provide controlled movement for the forearm.

It is yet another object of the present invention to provide an orthosis for an arm and shoulder which will fit the great majority of patients with a single left size and a single right size.

Other features, objects and advantages will become apparent from the specification and drawings.

BRIEF DESCRIPTION OF THE DRAWINGS

FIG. 4 is a frontal section through a pivoting slide, spacer block and angled bracket of the present invention, along the medio-lateral axial line A–A$_1$ of a lateral slide support.

FIG. 7 is an exploded left lateral perspective view of an alternative embodiment of the shoulder and arm orthosis, according to the present invention, with harness, belts, buckles, straps and linings omitted.

FIGS. 9a and 9b are left lateral perspective views of two alternative embodiments for providing optional controlled movement of the forearm.

DETAILED DESCRIPTION OF PREFERRED EMBODIMENTS

Figure 1:
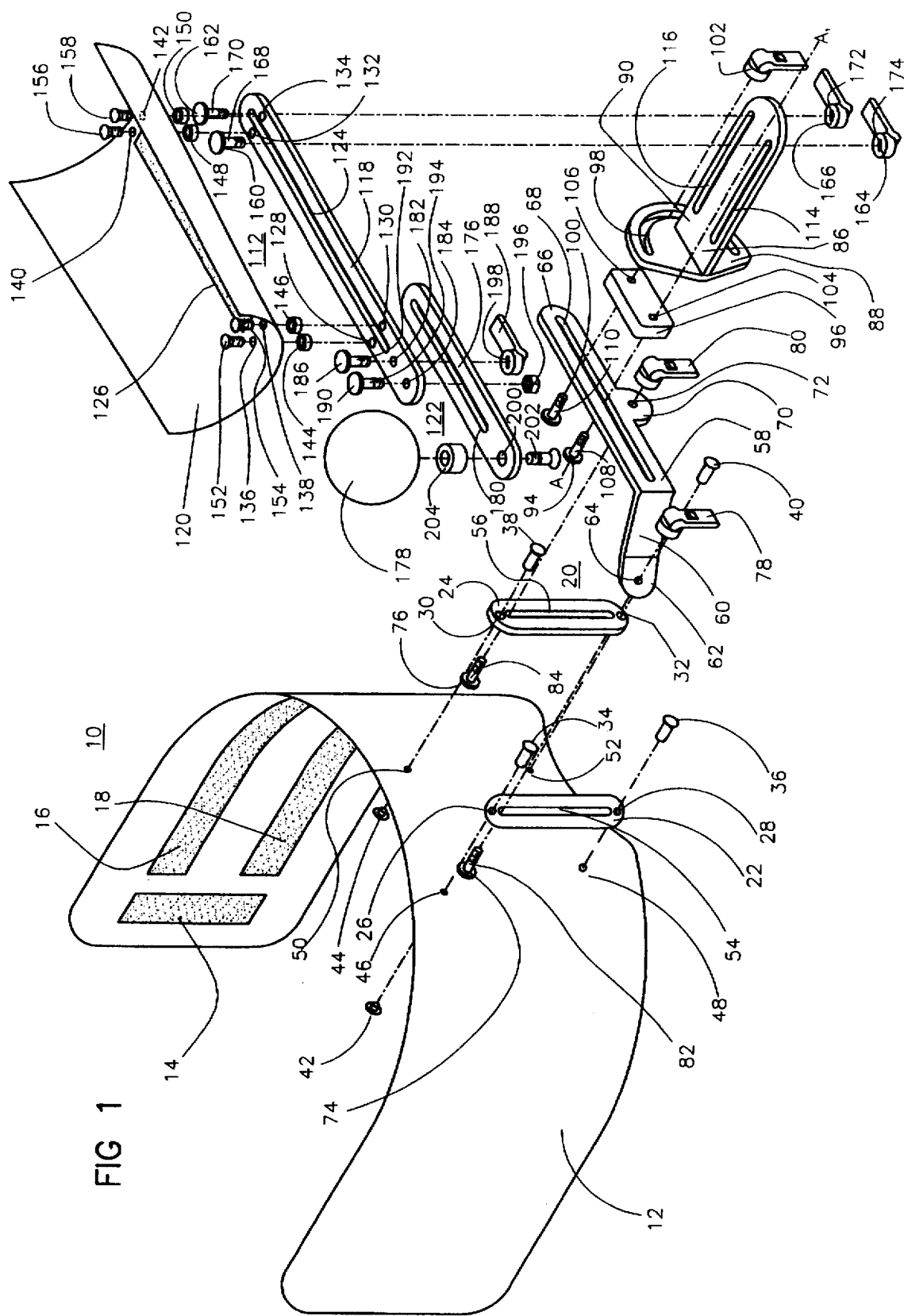
FIG. 1 is an exploded left lateral perspective view of a shoulder and arm orthosis, according to the present invention, showing the relationship between the various mechanical components but with the harness, bolts, buckles, straps and linings omitted.

Referring to the drawings FIGS. 1–8b and first with particular reference to FIGS. 1–4, there is shown an improved shoulder and arm positioning orthosis 10, according to the present invention, which does not require involvement of the upper trunk and axilla and which controls the position of the arm and shoulder joint, in a plurality of planes, in a novel manner. The particular orthosis 10, illustrated in the drawings, is adapted to serve the left shoulder and an orthosis, according to the invention, for the right shoulder will have its parts reversed or constructed as a mirror image of those shown for the left shoulder version.

Figure 3:
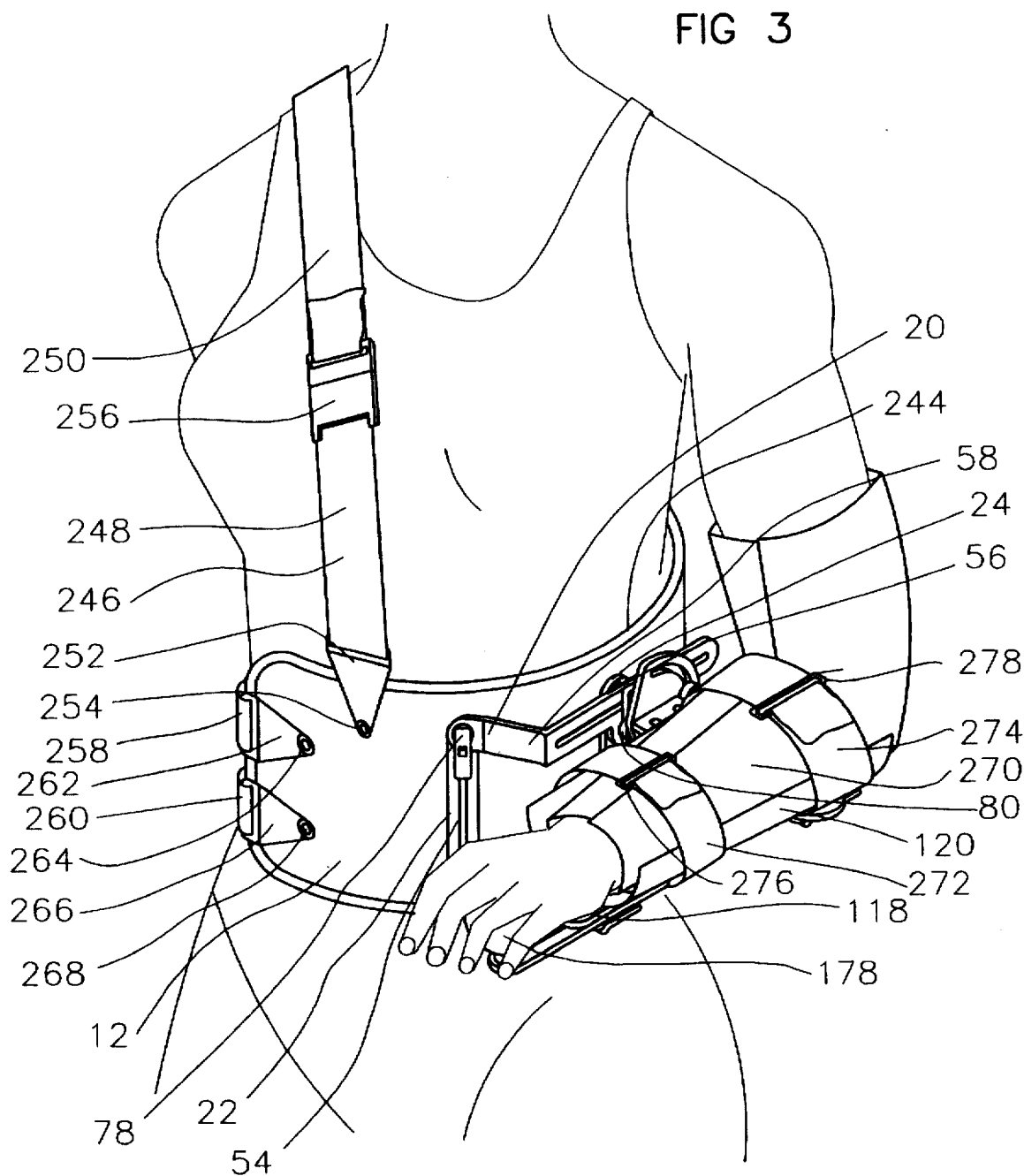
FIG. 3 is a left lateral perspective view of the complete shoulder and arm orthosis, according to the invention, in position on a human patient.

According to the invention, there is shown in FIG. 1, an orthosis 10 for immobilization of the human shoulder joint and arm in selected relative positions which has a semi-rigid and flexible waistband 12 preferably made in plastics such as polyethylene or polypropylene. Reference to FIG. 3, will indicate that waistband 12 is fitted with suitable securing and lining means, hereinafter described, for attachment to the waist and contra-lateral shoulder. Waistband 12 is of large surface area to provide mounting and load distributing means for orthosis 10. Downloading over an extensive area eliminates point loading which in turn improves patient tolerance. Waistband 12 has strips of self-adhesive hook-pile narrow fabrics 14, 16, and 18 attached to its inner surface.

Rise and fall mount means 20 for supporting other functional parts of orthosis 10 upon waistband 12 principally comprises three metal bars. These bars and all major metal components of orthosis 10 are preferably made in aluminum for lightness and strength. The first and second bars 22 and 24 are similar and are disposed on and spaced apart from waistband 12 in substantially parallel and vertical alignment, one laterally and the other somewhat anteriorly. Vertical bars 22 and 24 each have a top and bottom plain hole 26, 28 and 30, 32, respectively, for attachment to waistband 12 by means of screws 34, 35 and 38, 40 and internally threaded bushes (of which two, 42 and 44 may be seen in FIG. 1). The bushes are received through corresponding holes 45, 48 and 50, 52 in waistband 12. Each of vertical bars 22 and 24 has a slot 54 and 56, respectively, disposed centrally and extending over the greater parts of its length. The third bar is in the form of an asymmetrical, angled bracket 58. An anterior and medially directed portion 60 of angled bracket 53 is shorter and has an end portion 62 which is flared or bent away, antero-laterally, from the general line. End portion 62 has a plain hole 64 near its free end. A laterally disposed and antero-posteriorly directed portion 66 is longer and extends posteriorly, well past the lateral mid-line. Lateral portion 66 has a central slot 68 extending along the greater part of its length and is also provided with a short extension 70 from its lower margin, near its mid-point, which has a plain hole 72. Bolts 74 and 76 are received intimately and non-threadedly through plain holes 64 and 72 in angled bracket 58 and engage threadedly with lever-operated, pre-set, quick-release, over-center clamps 79 and 80. Plain portions 82 and 84 of bolts 74 and 76 also engage intimately and slidingly with slots 54 and 56 of vertical bars 22 and 24. When clamps 78 and 80 are securely closed they abut angled bracket 58. Clamps 78 and 80 and bolts 74 and 76 cooperate to secure angled bracket 58 to vertical bars 22 and 24 in a mutual and slidably adjustable manner.

Figure 2:
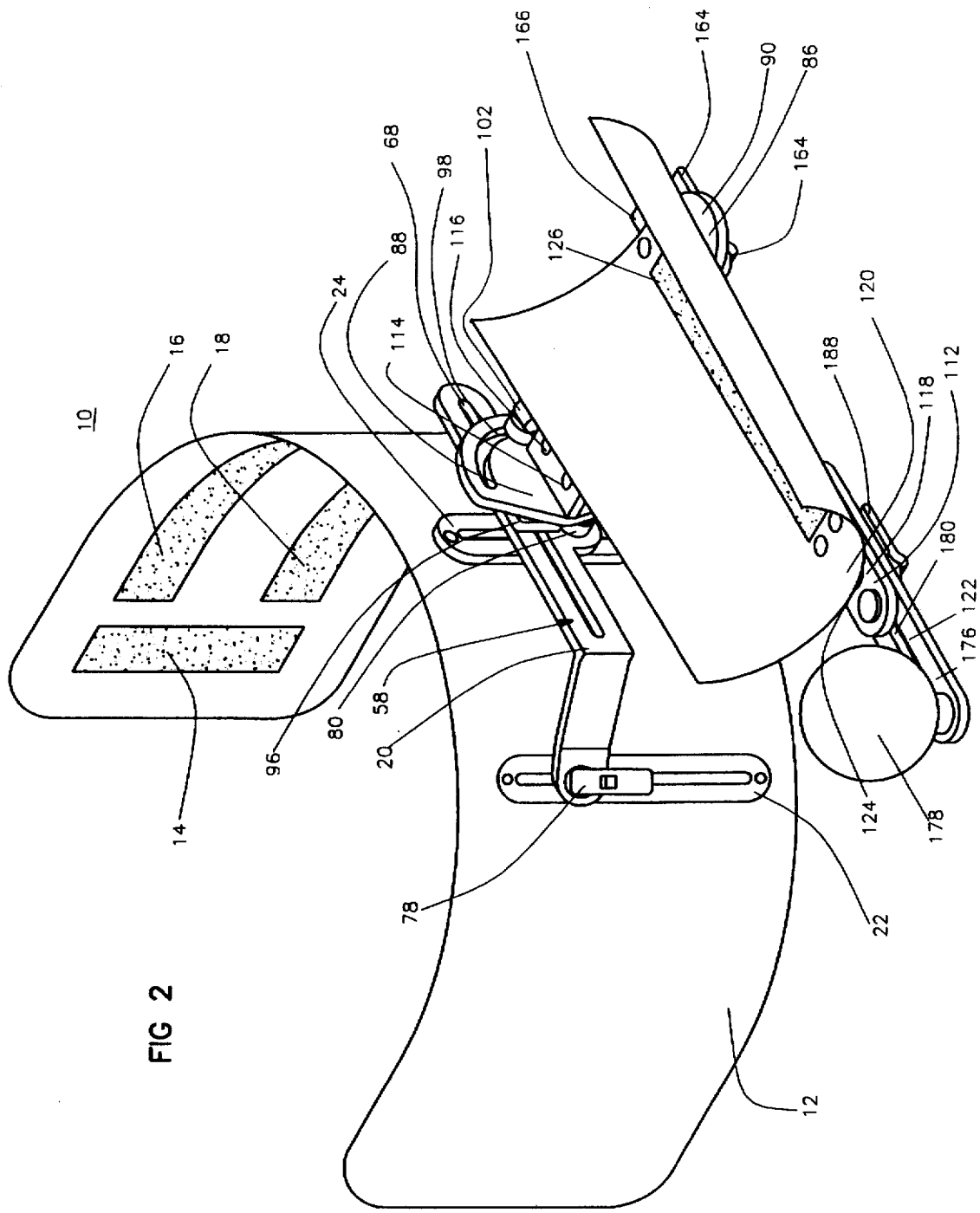
FIG. 2 is a left lateral perspective view of the shoulder and arm orthosis of FIG. 1, in the assembled condition.

As may be seen by reference to FIGS. 2 and 3, when so secured, angled bracket 58 is disposed in a substantially horizontal manner in relation to a standing patient. The cooperative arrangement of angled bracket 58, adjustably and slidably secured to slots 54 and 56 of vertical bars 22 and 24, constitutes a stable rise and fall mount 20 which may be located at any position within slots 54 and 56. By slackening clamps 78 and 80, other elements of orthosis 10 and an arm held within it may be moved slidingly, in a continuously variable manner, up or down slots 54 and 56 to a selected position in the vertical plane, after which clamps 78 and 80 are re-secured. All clamps used in the preferred embodiment are of a lever-operated, pre-set, quick-release, over-center type described hereinafter with reference to FIGS. 5, 6a and 6b.

A metal pivoting slide 86, mounted upon rise and fall mount 20 and extending laterally from it, has a short, generally vertically disposed portion, constituting a pivoting plate 88 and a longer, laterally disposed portion, constituting a lateral slide support 90. As may be seen by reference to FIG. 4, with continuing reference to FIG. 1, pivoting plate 88 has a threaded hole 92, the axis of which lies on the medio-lateral axis A—A, of lateral slide support 90. A pivot bolt 94, received non-threadedly through a spacer block 96 and threadedly into hole 92 secures pivoting plate 88 pivotally and non-releasably to angled bracket 58, these elements being held in sliding contact. The engagement between pivot bolt 94 and threaded hole 92 is precisely set during assembly and the sparing use of an anaerobic setting, resin based or similar thread-locking compound on the threads ensures that the pre-set level of contact between the cooperating elements will not be lost during subsequent adjustment of pivoting plate 88.

As best seen in FIGS. 1 and 2, pivoting plate 88 has an arcuate slot 98, concentric with the axis of pivot bolt 94 and which extends over at least 180° of arc. Arcuate slot 98 receives a bolt 100 non-threadedly, intimately and slidably, for threaded attachment of a clamp 102. When clamp 102 is in the secured position, it abuts pivoting plate 88. Spacer block 96, disposed between pivoting plate 88 and angled bracket 58 has plain holes 104 and 106 for the intimate receival of plain portions 108 and 110 of pivot bolt 94 and clamp attachment bolt 100, respectively. Spacer block 96 ensures that clamp 78, acting on extension 70 of angled bracket 58, may be operated without interfering with other parts of the mechanism. Plain portions 108 of pivot bolt 94 and 110 of clamp attachment screw 100 are also mutually, slidably and intimately engaged with slot 68 in angled bracket 58.

Pivoting slide 86, pivot bolt 94, clamp 102 and clamp attachment bolt 100, together with spacer block 96, cooperate with slot 68 in angled bracket 58 to provide anteroposterior and pivotal adjustment means for a forearm support assembly 112 (hereinafter described), mounted upon lateral slide support 90. By slackening clamp 102, pivoting slide 86 and hence forearm support assembly 112, together with spacer block 96, may be moved, in a continuously variable manner, to any selected point along slot 68 of angled bracket 58, after which clamp 102 is resecured. In addition and by the same action with regard to clamp 102, pivoting slide 86 and forearm support assembly 112, may be moved, pivotally, in a continuously variable manner, about the axis of pivot bolt 94, within the very wide limits of arcuate slot 98, to provide a plurality of scandent and dependent positions for a human forearm. By these means, the elbow and forearm may be moved to any position between fully extended and fully flexed and hence the shoulder may be placed in internal rotation or external rotation.

The elbow is a pivot joint and the instant invention provides novel means for the natural axis of flexion and extension of the elbow to be placed substantially on the pivoting axis of pivoting slide 86. This avoids the compount adjustment of shoulder joint position when the elbow position is altered which occurs with prior art orthoses which employ an adjustment for elbow flexion and extension which is placed at a distance from the anatomical elbow axis.

Lateral slide support 90 has two, substantially parallel, widely spaced slots 114 and 116, extending along most of its length and disposed equidistant about the mid-line. Forearm support assembly 112 comprises a metal travelling support bar 118, a forearm retaining shell 120 and a hand support assembly 122. Travelling support bar 118 has a slot 124, disposed centrally along the greater part of its length. Forearm retaining shell 120 is made in plastics and is provided with a self-adhesive strip of hook pile narrow fabrics 126 centrally along its concave upper surface. Travelling support bar 118 also has a pair of threaded holes 128, 130 and 132, 134 at each end, respectively. Forearm retaining shell 120 has corresponding holes 136, 138 and 140, 142 (the last of these being represented in hidden detail in FIG. 1) which are preferably countersunk. Spacer brushes 144, 146 and 148, 150, space forearm retaining shell 120 apart from travelling support bar 118 and countersunk screws 152, 154 and 156, 158 secure these elements together, non-releasably. Screws 152, 154 and 156, 158 pass non-threadedly through holes 136, 138 and 140, 142 and spacer brushes 144, 146 and 148, 150 and are received threadedly into holes 128, 130 and 132, 134.

Longitudinal slot 124 in travelling support bar 118 and slots 114 and 116 of lateral slide support 90, receive bolts 160 and 162 non-threadedly. Bolts 160 and 162 also engage threadedly and non-releasably with clamps 164 and 166, respectively, to secure travelling support bar 118 and lateral slide support 90, together in a slidable relationship. Whereas plain portions 168 and 170 of clamp bolts 160 and 162, engage intimately and slidingly with slot 124 in travelling support bar 118, their engagement with slots 114 and 116 is sliding and non-intimate. When clamps 164 and 166 are tightened, their respective faces 172 and 174 abut the underside of lateral slide support 90, locking it to forearm support assembly 112.

Slots 114 and 116 of lateral slide support 90, slot 124 of traveling support bar 118, clamp bolts 160 and 162, together with clamps 164 and 166, cooperate to provide a wide range of slidable and lockable adjustment for forearm support assembly 112. As may best be understood by reference to FIGS. 1 and 2, when clamps 164 and 166 are slackened, travelling support bar 118 and hence an arm secured within forearm retain shell 120, may be moved, in a continuously variable manner, towards or away from the body over the length of slots 114 and 116. Thus the shoulder joint may be adducted or abducted to a required position where it may be securely positioned by re-tightening clamps 164 and 166. The length of slots 114 and 116 and the vertical adjustment range of rise and fall mount 20 are so selected that 45° of abduction may readily be achieved in the great majority of patients. Additionally, with clamps 164 and 166 slackened, travelling support bar 118 may be slid anteriorly or posteriorly along the full extent of its slot 124. Furthermore, the anterior end of travelling support bar 118 may be swung, slidingly, in towards the body through a wide angle, or vice versa. These latter movements may be accomplished more or less regardless of where travelling support bar 118 is placed in relation to lateral slide support 90.

This great range of positional possibilities and their easy accomplishment in a non-binding manner is achieved by means of the non-intimate sliding relationship between clamp bolts 160 and 162 and slots 114 and 116 of lateral slide support 90 and their intimate sliding relationship with slot 124 of the travelling support bar 118.

A further advantage of the instant invention is that the relatively wide dimension of lateral support slide 90 and the wide spacing of its slots 114 and 116 provides a more stable platform for a forearm support assembly than is possible with prior art orthoses employing circular spigot type or ball joint lateral mounts.

A hand support assembly 122 has a hand support bar 176 and a hand support 178. Hand support bar 176 is similar in plan view but shorter in length than travelling support bar 118 and has a centrally disposed longitudinal slot 180. Travelling support bar 118 has two plain holes 182 and 184 in the mid-line near its anterior end, distal to slot 124. Hole 182 receives a bolt 186 for attachment of a clamp 188. Hole 184 receives a retaining bolt 190. Plain portions 192 and 194 of clamp bolt 186 and retaining bolt 190, respectively, pass intimately through distal holes 182 and 184 and engage intimately and slidingly with slot 180 of hand support bar 176. Clamp bolt 186 and retaining bolt 190, engage threadedly and non-releasably with clamp 188 and a lock nut 196, respectively, to secure travelling support bar 118 to hand support bar 176. The extent of engagement between retaining bolt 190 and lock nut 196 is controlled during assembly in the same manner and with the same object as that between pivot bolt 94 and pivoting plate 88.

When clamp 188 is tightened, its face 198 abuts the underside of hand support bar 176, locking it against travelling support bar 188. Hand support bar 176 has a plain hole 200 on its mid-line and close to its distal margin which accommodates a screw 202 for attachment to its upper aspect, of a spacer bush 204 and hand support 178. Hand support 178 is preferably spherical and has suitable thread means for threaded engagement by screw 202.

Hand support 178, hand support bar 176, travelling support bar 118, clamp 188, clamp bolt 186, retaining bolt 190 and nut 196, cooperate to provide continuously variable, slidable adjustment means for comfortable positioning for the hand and wrist.

Figure 6A:
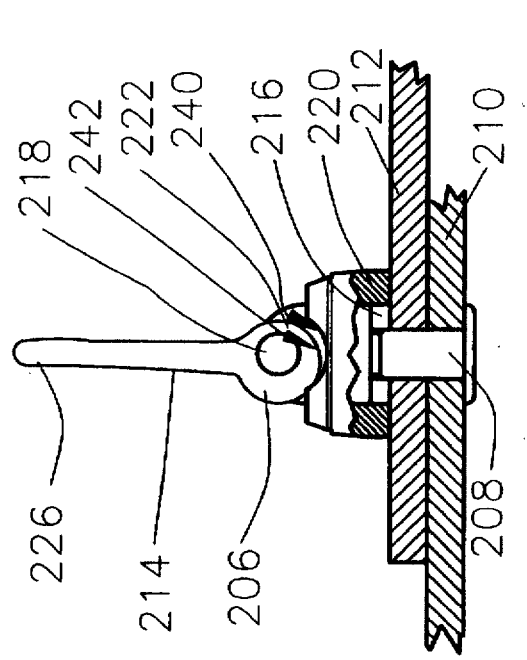
FIGS. 6a and 6b are partial sections of the assembled clamp and cooperating parts of FIG. 5, shown in the open (released) and closed (tightened or secured) positions, respectively.
Figure 6B:
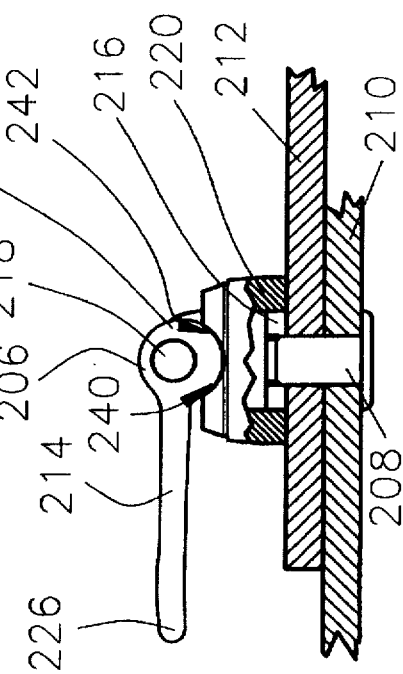
Figure 5:
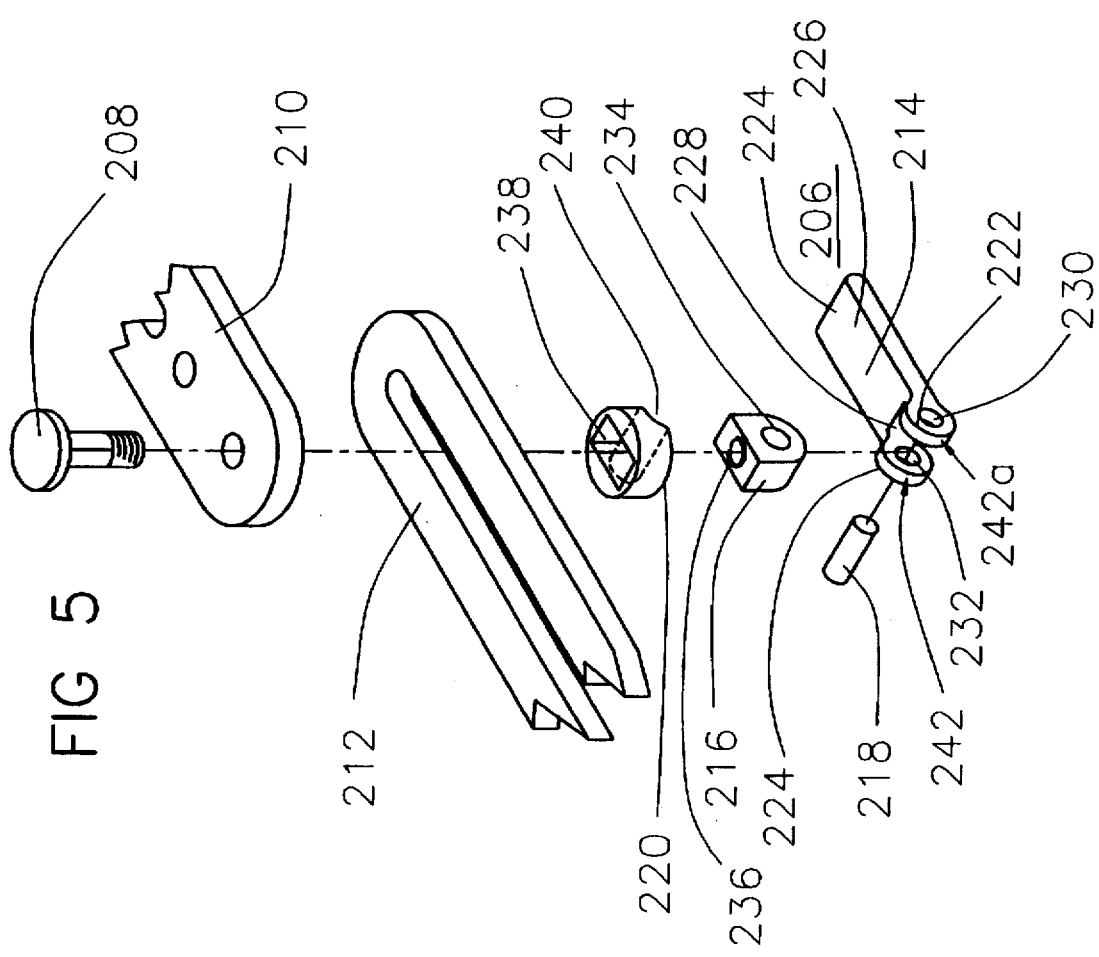
FIG. 5 is an exploded perspective view of a lever-operated, quick-release, over-center clamp of a type preferred in the present invention, together with relevant cooperating parts.

Turning now to FIGS. 5, 6a and 6b, the construction of clamps 78, 80, 102, 164, 166 and 188 and their relationship with respective attachment bolts 74, 76, 100, 160, 162 and 186 may be illustrated generically.

A lever-operated, pre-set, quick-release, over-center clamp 206 is made of metal and is threadedly and non-releasably engaged by a bolt 208. Clamp 206 and bolt 208 cooperate to secure together first and second bars 210, 212 disposed in a substantially parallel manner between them. Clamp 206 comprises an operating member 214, which is secured to an actuator member 216 by a pin 218 and operates against a pressure plate 220. Operating member 214 has cam portions 222 and 224 and a lever portion 226. Cam portions 222 and 224 are disposed to form a yoke 228, for the receival of actuator member 216 which is rectangular in plan. Cam portions 222 and 224 are provided with transverse through holes 230 and 232. Pin 218 is a firm press-fit within holes 230 and 232 and an easy sliding fit through a transverse plain first hole 234 in actuator member 216. Actuator member 216 has a blind, threaded, second hold 236 in its base for the threaded receival of bolt 208. Pressure plate 220, which is preferably molded from fiberglas reinforced plastics, has the form of a disk with a central rectangular through-aperture 238 for the sliding engagement of actuator member 216. Pressure plate 220 is also provided with a recess 240 on its upper surface (seen partly in hidden detail in FIG. 5). Recess 240 has an arcuate profile and lies along a diameter substantially parallel to the short sides of aperture 238.

In the assembled condition, the common profiles of cam portions 222 and 224 of operating member 214, indicated at 242 and 242a, respectively, are received into recess 240 of pressure plate 220. When clamp 206 is in the released condition, which occurs when lever portion 226 of operating member 214 is lifted away from pressure plate 220 (FIG. 6a), bars 210 and 212 are held in easy sliding contact. When lever portion 226 of operating member 214 is moved towards pressure plate 220 (FIG. 6b), cam portions 222 and 224 operate against recess 240 of pressure plate 220 to induce a large compressive force between bars 210 and 212, sufficient to prevent movement between them at physiological loads. Common cam profiles at 242 and 242a are preferably of the over-center type, so shaped that the compressive force at first increases gently to allow the operator an element of fine control over the decision as to final locked placement of bars 210 and 212. Continued operation of lever portion 226 causes the compressive force to increase rapidly to a maximum until the over-center region of the profiles is reached, at which point the clamp is parked in a stable, locked position with lever portion 226 substantially parallel to the principal plane of bars 210 and 212.

Management of the sliding contact in the released condition and the clamping force in the closed or secured condition is achieved by careful selection of the length of bolt 208 and the extent of its engagement with blind threaded hole 236 of actuator member 216. The precise extent of this engagement is determined and set during assembly. The sparing use of an anaerobic setting, resin based or similar thread-locking compound on the threads of bolt 208 ensures that the level of clamping force when closed and the degree of sliding contact when in the released condition between the cooperating elements will not be lost during subsequent use of clamp 206.

Returning to FIG. 3, it may be seen that waistband 12 is provided with a soft pad liner 244, which is substantially the same shape and slightly larger. Loads developed within orthosis 10 are transmitted to waistband 12 and are then distributed over an extensive area of soft tissue about the iliac crest and around the abdomen and upper buttock. Waistband 12 is large in order to diminish point loading and liner 244 further enhances comfort. Liner 244 is preferably made from foamed, open-cell plastics, lined internally with terry toweling or chamois leather and externally with brushed narrow fabrics 14, 16 and 18 provided on the inner aspect of waistband 12 and previously described with reference to FIGS. 1 and 2. A harness 246 comprises straps 248 and 250, each secured to waistband 12 with a loop-ring fitting and a rivet. Loop-ring fitting 252 is secured, pivotally, to waistband 12 at a front point near the mid-line, just ipsilateral with the shoulder under treatment by rivet 254. Harness 246 passes upwards and over the contra-lateral shoulder, then down and across the back to a second, just ipsilateral, rear attachment (not seen) which is substantially similar to that provided by 252 and 254. A buckle 256 is attached to straps 248 and 250 and provides for adjustment of the effective length of harness 246 by means of which almost any size of patient may be fitted. The primary function of harness 246 is to impart rotational stability to waistband 12 and hence to the entire orthosis 10. Waistband 12 is secured to the patient's waist with front belt portions 258 and 260 which are each attached at the front by means of loop-rings and rivets 262, 264 and 266, 268, respectively. Rear belt portions, loop-ring and rivet attachments and buckles are not seen in FIG. 3 but are in all respects intended to be similar to those already described.

A soft pad liner 270 is also provided for the arm within forearm retaining shell 120 and is so sized and shaped as to extend from the wrist to somewhat above the elbow. Liner 270 is preferably of similar construction to liner 244 and attaches to strip of hook pile narrow fabrics 126 previously described with reference to FIGS. 1 and 2. Straps 272 and 274 are each secured at one end to a slip-ring 276 and 278, respectively, and are routed between forearm retaining shell 120 and traveling support bar 118 to pass around the arm and liner 270 so as to provide comfortable securing and immobilizing means for the forearm within orthosis 10.

It is to be understood that, although preferred, this construction and arrangement of liners, straps, belts, buckles and rings is not of the essential essence of the invention.

It will now be understood that within the present invention, the mechanical and geometrical relationship between the components of rise and fall mount 20, pivoting slide 86 and the forearm assembly 112, particular the slots 54, 56, 68, 98, 114, 116, 124 and 180, therein, together with the provision of lever operated, pre-set, quick-release, over-center clamps 78, 80, 102, 164, 166, 188 and their respective attachment bolts 74, 76, 100, 160, 162 and 186, is so arranged that positioning of the shoulder joint in flexion, extension, internal and external rotation abduction and adduction or combinations thereof, may be achieved over a large angular range and in a continuously variable, stable and easy manner. In particular and in contrast to prior art orthoses, these adjustments may be accomplished over their full range more or less regardless of trunk length and humerus length. Furthermore, the components are so sized that mutual, continuously variable, adjustment between them is available over a very wide range of patient sizes and shapes with a single orthosis for the right arm and shoulder and a single orthosis for the left arm and shoulder.

OTHER PREFERRED EMBODIMENTS

Figure 8:
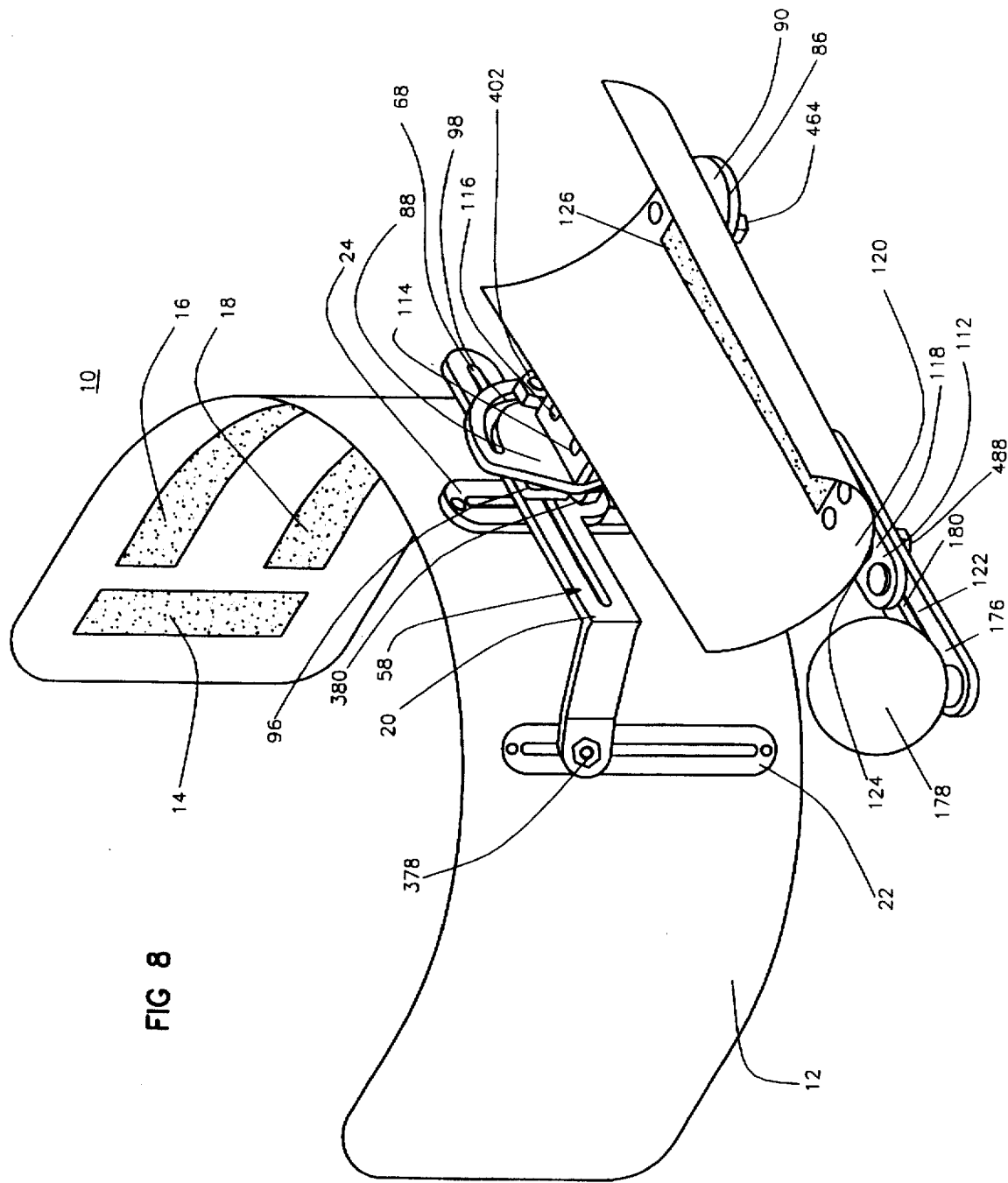
FIG. 8 is a left lateral perspective view of the alternative embodiment of the shoulder and arm orthosis of FIG. 6, in the assembled condition.

In FIGS. 7 and 8, there is illustrated another preferred embodiment of the present invention which is similar in all essential respects to the first preferred embodiment except that locking nuts 378, 380, 402, 464, 466 and 488 are employed instead of lever-operated, pre-set, quick-release, over-center clamps. This confers the advantage of lower manufacturing cost at the expense of a degree of speed and ease of adjustment. However, when dealing with patients who may be judged likely to interfere with the settings, this arrangement has advantages. Security against interference from patients may be further enhanced by the use of non-standard nuts since this embodiment requires availability of a suitable wrench in order to make adjustments. It is preferable in this embodiment that bolts 74, 76, 100, 160, 162 and 186 have plain under-head portions with at least one pair of flats and that hole 106 through spacer block 96, is of substantially similar cross section. Lock nut 402 and screw 100 are provided with means to ensure that the former will not migrate spontaneously. This may optionally be achieved by the use of a resin patch on the threads of screw 100 or selecting nut 402 to be of a type fitted with an internal nylon locking ring; we prefer the latter.

Two further embodiments are shown in FIGS. 9a and 9b, both of which provide means for allowing controlled movement of the forearm in the vertical plane over a selected range of motion. The adjustment and motion limiting means involve modifications which affect only pivoting plate 88 of pivoting slide 86 of the first embodiment.

In FIG. 9a, which is a development from the embodiment of FIGS. 7 and 8, an integrally collared lock nut 500 is threadedly engaged by bolt 100 and is provided with a nylon locking ring (not seen) to ensure that it will not migrate spontaneously. Two additional integrally collared lock nuts 502 and 504 are threadedly engaged by short bolts 506 and 508, respectively. Bolts 506 and 508 have plain under-head portions (not seen) with at least one pair of flats which engage arcuate slot 98 in pivoting plate 88, in a manner which, when not tightened down, allows an easy sliding fit but which will not allow rotation. When pivoting slide 86 is required to be used in a fixed mode, it may be locked in the selected position simply by tightening lock nut 500 with a suitable wrench; bolts 506 and 508 with lock nuts 502 and 504 are loosened and moved, together with their respective bolts 506 and 508, to the required stop positions within arcuate slot 98, whereupon they are re-tightened. Lock nut 500 is then slackened until sliding motion within arcuate slot 98 becomes available. The order of adjustments may, of course, be varied according to choice. During controlled motion, collars 510 and 512 of bolts 506 and 508, form abutment stops which act against collar 514 of lock nut 500, to limit travel of pivoting plate 88 which is part of pivoting slide 86.

In FIG. 9b, which is also a development from the embodiment of FIGS. 7 and 8, an integrally collared lock but 500 is threadedly engaged by bolt 100, as described with reference to the embodiment of FIG. 9a. Two lever-operated, pre-set, quick-release, over-center clamps 516 and 518, are threadedly engaged by short bolts 506 and 508 (not seen) also as previously described. In this embodiment, pressure plates 520 and 522 of clamps 516 and 518 function as the upper and lower abutment stops. The use of clamps 516 and 518 makes setting of the range of motion stops quicker and easier. The use of a clamp instead of a collared lock nut 500 has not been found satisfactory since, in order to allow motion within arcuate slot 98, the clamp must be in the released position and this allows the lever portion to be moved with the risk of occasionally fouling the mechanism and inadvertent re-tightening.

The preferred embodiments have been described with a view to illustration of the elements of the present invention rather than limitation. Other variations and modifications to the disclosed embodiments which do not depart from the intended spirit and scope of the invention will be apparent to those skilled in the art. Such modifications are intended to be encompassed within the present invention.

I claim:

1. An orthosis for immobilizing the shoulder joint and arm of a human patient in selected relative positions comprising attaching means for attaching said orthosis securely to a patient's waist; mounting means secured to said attaching means providing a pair of parallel and generally vertical slots; an antero-posteriorly extending bracket equipped with releasable securing means extending through said slots for infinite variable positioning of said bracket along said slots; said bracket having an antero-posteriorly extending slot; an arm support assembly for supporting a patient's arm; and slide means adjustably connecting said arm support assembly and said bracket for securing said arm support assembly into any selected position along the length of said bracket slot.

2. The orthosis of claim 1 in which said slide means includes a pivot plate connected to said bracket for pivotal movement of said plate about a generally horizontal axis perpendicular to said bracket slot.

3. The orthosis of claim 1 in which said pivot plate includes a lateral slide support extending in a generally horizontal direction away from said plate; said slide support having at least one slot extending along its length; said arm support assembly being provided with mounting means for securing said assembly in any selected position along the length of said slot of said slide support.

4. The orthosis of claim 1 in which said mounting means secured to said attaching means comprises two generally vertically extending slotted members secured to said attaching means.

5. The orthosis of claim 4 wherein said bracket is angled and includes an antero-posteriorly directed portion and a medially directed portion; said antero-posteriorly directed portion being attached to one of said slotted members and said medially directed portion being attached to the other of said slotted members.

* * * * *